United States Patent
Kawakami et al.

(10) Patent No.: US 9,161,867 B2
(45) Date of Patent: Oct. 20, 2015

(54) WEARING ARTICLE

(71) Applicant: UNICHARM CORPORATION, Ehime (JP)

(72) Inventors: Yusuke Kawakami, Kagawa (JP); Kazuya Fujimoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/397,448

(22) PCT Filed: May 15, 2013

(86) PCT No.: PCT/JP2013/063605
§ 371 (c)(1),
(2) Date: Oct. 27, 2014

(87) PCT Pub. No.: WO2013/172393
PCT Pub. Date: Nov. 21, 2013

(65) Prior Publication Data
US 2015/0088087 A1     Mar. 26, 2015

(30) Foreign Application Priority Data

May 15, 2012 (JP) .................................. 2012-111951
Nov. 9, 2012 (JP) .................................. 2012-247919

(51) Int. Cl.
*A61F 13/15* (2006.01)
*A61F 13/514* (2006.01)
*A61F 13/49* (2006.01)
*A61F 13/496* (2006.01)
(Continued)

(52) U.S. Cl.
CPC ..... *A61F 13/51496* (2013.01); *A61F 13/15203* (2013.01); *A61F 13/496* (2013.01);
(Continued)

(58) Field of Classification Search
CPC .................. A61F 13/49007; A61F 13/49009; A61F 13/49011; A61F 13/49019; A61F 13/49058; A61F 13/4906; A61F 13/49061; A61F 13/49413; A61F 13/4942; A61F 2013/49025
See application file for complete search history.

(56) References Cited

U.S. PATENT DOCUMENTS

2003/0045855 A1 * 3/2003 Ono et al. ................... 604/387
2012/0165774 A1 6/2012 Otsubo et al.
(Continued)

FOREIGN PATENT DOCUMENTS

JP     2002-000657 A     1/2002
JP     2009-254597 A     11/2009
(Continued)

OTHER PUBLICATIONS

International Search Report from corresponding PCT application No. PCT/JP2013/063605 dated Jul. 16, 2013 (2 pgs).

*Primary Examiner* — Lynne Anderson
(74) *Attorney, Agent, or Firm* — Brinks Gilson & Lione (57) ABSTRACT

A wearing article including a region in which the wearer's skin is not seen-through other than the existence region of the absorbent structure even when an area of the absorbent structure is relatively small so that the existence region of the absorbent structure may be un noticeable from the outside. A region of the absorbent structure of a diaper overlapping with the first waist region has a dimension in the transverse direction corresponding to 20 to 30% of a dimension in the transverse direction of the first waist region, the first waist region is disposed with a hardly see-through panel overlapping with the absorbent structure and includes a first region in which the chassis, the absorbent structure and the hardly see-through panel are laminated, second regions adjacent on both outsides in the transverse direction of the first region, in which the chassis and the hardly see-through panel are laminated and third regions adjacent on both outsides in the transverse direction of the respective second regions and only the chassis is included; and a differential total luminous transmittance between the first region and the second regions is smaller than a differential total luminous transmittance between the second region and the third region.

20 Claims, 5 Drawing Sheets

(51) Int. Cl.
*A61F 13/494* (2006.01)
*A61F 13/515* (2006.01)
*A61F 13/84* (2006.01)

(52) U.S. Cl.
CPC ..... *A61F13/49011* (2013.01); *A61F 13/49061* (2013.01); *A61F 13/49413* (2013.01); *A61F 13/515* (2013.01); *A61F 13/51478* (2013.01); *A61F 2013/15243* (2013.01); *A61F 2013/4948* (2013.01); *A61F 2013/49068* (2013.01); *A61F 2013/49092* (2013.01); *A61F 2013/8497* (2013.01)

(56) References Cited

U.S. PATENT DOCUMENTS

2012/0283682 A1* 11/2012 Otsubo et al. ............ 604/385.01
2014/0142531 A1* 5/2014 Sasayama et al. ....... 604/385.21

FOREIGN PATENT DOCUMENTS

JP 2011-067602 A 4/2011
JP 2011-224404 A 11/2011

* cited by examiner

WEARING ARTICLE

RELATED APPLICATION

This application is a 35 U.S.C. §371 national phase filing of International Patent Application No. PCT/JP2013/063605, filed May 15, 2013, through which and to which priority is claimed under 35 U.S.C. §119 to Japanese Patent Application Nos. 2012-111951, filed May 15, 2012 and 2012-247919, filed Nov. 9, 2012, the complete disclosures of which are hereby expressly incorporated herein by reference.

TECHNICAL FIELD

The present disclosure relates to wearing articles and particularly to wearing articles each including a chassis with relatively high total luminous transmittance and an absorbent structure, for example, diaper, toilet-training pants, incontinent pants, sanitary pants and absorptive pads.

BACKGROUND

Conventionally, disposable wearing articles are known having an absorbent structure attached to the skin-facing surface of a chassis. For example, Patent Literature 1 discloses a disposable wearing article including a chassis formed from a fibrous nonwoven fabric so as to define front and rear waist regions and a crotch region and an absorbent structure attached to a skin-contact surface of the chassis so as to extend across the crotch region into the front and rear waist regions. Total luminous transmittance of the fibrous nonwoven fabric forming the chassis is set relatively high so that a picture on film may be visually recognized even through the fibrous nonwoven fabric.

CITATION LIST

Patent Literature

{PTL 1}: JP 2002-657 A

SUMMARY

Technical Problem

For the disposable wearing article disclosed in Patent Literature 1, the total luminous transmittance of the chassis is set relatively high and, in consequence, the wearer's skin may be seen through the chassis in a region of the chassis overlapping with neither the film nor the absorbent structure. Particularly when an area of such see-through region is distinctively large relative to an area of the chassis, the wearer might be forced to have a sense of embarrassment. In addition, particularly when an area of the absorbent structure is dimensioned to be further smaller relative to an area of the chassis, the wearer might be driven by a sense of anxiety with respect to leakage of body exudates. Furthermore, if a boundary between the existence region and the non-existence region of the absorbent structure is visually recognizable too distinctly, the existence region of the absorbent structure might distinguish itself and create a feeling of strangeness from the standpoint of appearance.

An object of the present invention is to improve the conventional wearing article and to provide a wearing article including a region in which the wearer's skin is not seen-through other than the existence region of the absorbent structure even when an area of the absorbent structure is relatively small so that the existence region of the absorbent structure may be un noticeable from the outside.

Solution to Problem

The present invention relates to an improvement in a wearing article having a longitudinal direction and a transverse direction being orthogonal to the longitudinal direction and including a chassis having a skin-facing surface and a non-skin-facing surface lying on a side opposite to the skin-facing surface, a first waist region corresponding to any one of front and rear waist regions, a second waist region corresponding to another of the front and rear waist regions and a crotch region extending between the first and second waist regions and an absorbent structure located on the skin-facing surface of the chassis and extending in the longitudinal direction across the absorbent structure at least into the first waist region.

In such wearing article, the present invention is lies in that a region of the absorbent structure overlapping with the first waist region has a dimension in the transverse direction corresponding to 20 to 30% of a dimension in the transverse direction of the first waist region; the first waist region is provided with a hardly see-through panel overlapping with the absorbent structure and includes a first region in which the chassis, the absorbent structure and the hardly see-through panel are laminated, second regions adjacent on both outsides in the transverse direction of the first region, in which the chassis and the hardly see-through panel are laminated and third regions adjacent on both outsides in the transverse direction of the respective second regions and only the chassis is included; and a differential total luminous transmittance between the first region and the second regions is smaller than a differential total luminous transmittance between the second region and the third region.

Advantageous Effects of Invention

According to one or more embodiments of the present invention, in the first waist region, the second region provided with the hardly see-through panel adjacently lies on the outsides in the transverse direction of the first region in which the absorbent structure exists. With such an arrangement, it is possible to prevent the wearer's skin from being seen through from the outside over a relatively wide range. In addition, the differential total luminous transmittance between the first region and the second region is smaller than the differential total luminous transmittance between the second range and the third range defined by the chassis alone and adjacently lying on the outer side of the second region in the transverse direction. Consequently, it is unlikely that a boundary between the existence region and the non-existence region of the absorbent structure might distinguish itself and cause disfigurement.

DESCRIPTION OF EMBODIMENTS

Figure 1:
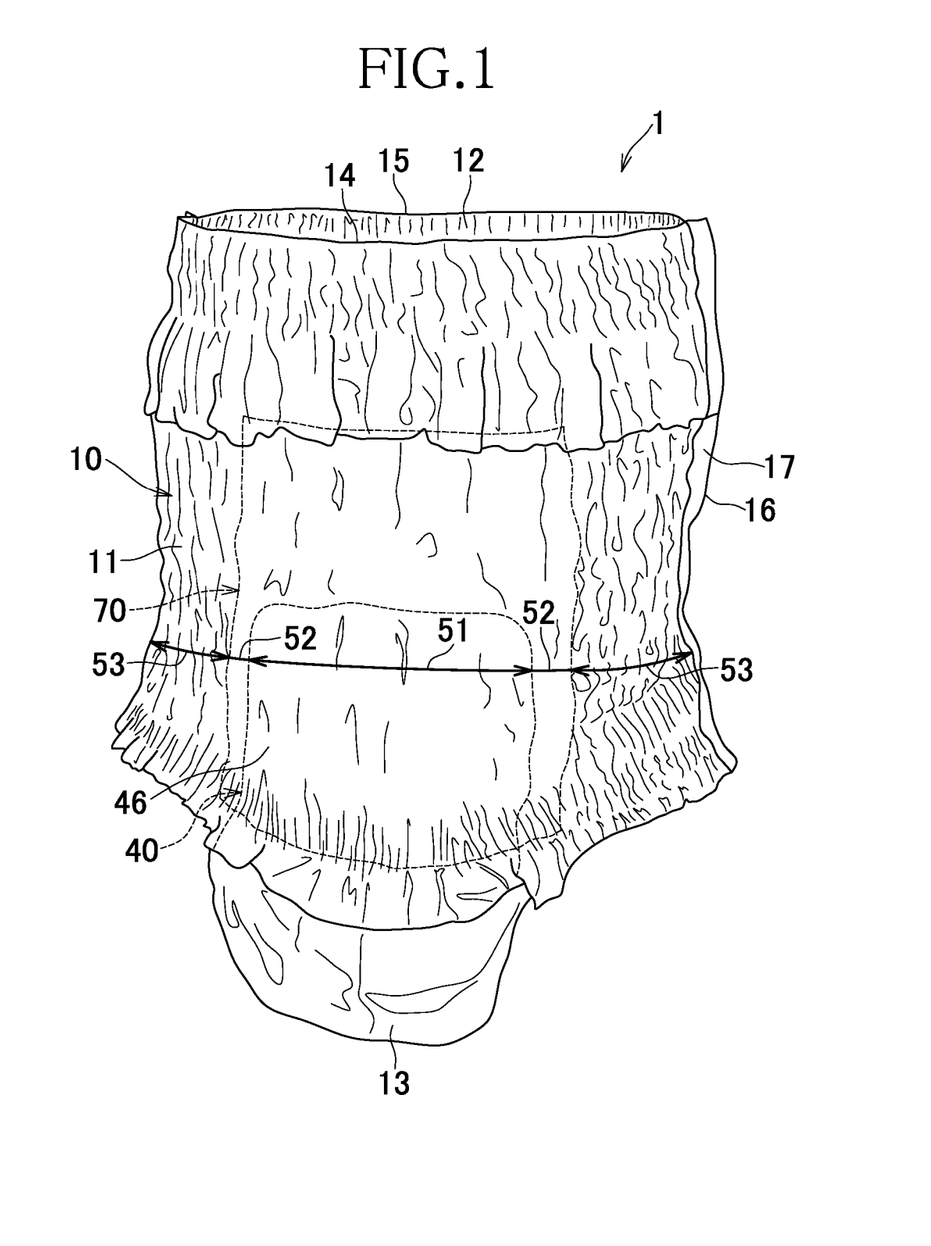
FIG. 1 is a perspective view of a diaper as an example of a wearing article according to the present invention as viewed from a front waist region side.

Referring to FIG. 1, a diaper 1 in the form of a disposable diaper as an example of a wearing article has a wearer's skin-facing surface and a non-skin-facing surface lying on the opposite side and includes a chassis 10, an absorbent structure 40 located on the skin-facing surface of the chassis 10 and a hardly see-through panel 70 overlapping with a part of the absorbent structure 40. The chassis 10 has a front waist region (on of first and second waist regions) 11, a rear waist region (the other of the first and second waist regions) 12, a crotch region 13 extending between the front and rear waist regions 11, 22, front and rear end portions 14, 15 extending in a transverse direction X and both side edges extending in a longitudinal direction Y. Along both side edges 16, seams continually extending in the longitudinal direction Y are formed along which the front and rear waist regions 11, 12 are joined to each other so that a waist-opening may be defined by the front and rear end portions 14, 15 and leg-openings may be defined by both side edges in the crotch region 13.

Figure 2:
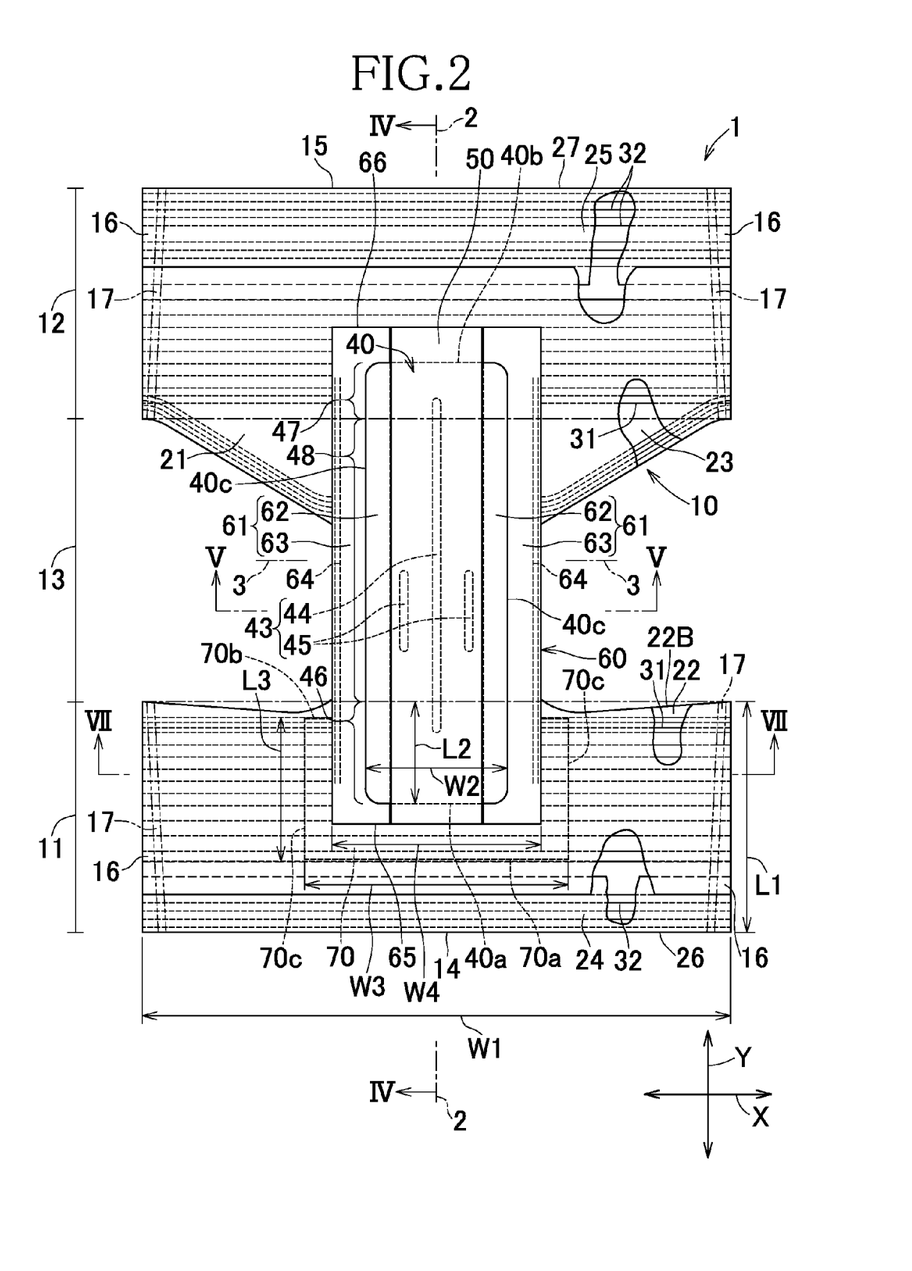
FIG. 2 is a developed plan view of the diaper.
Figure 3:
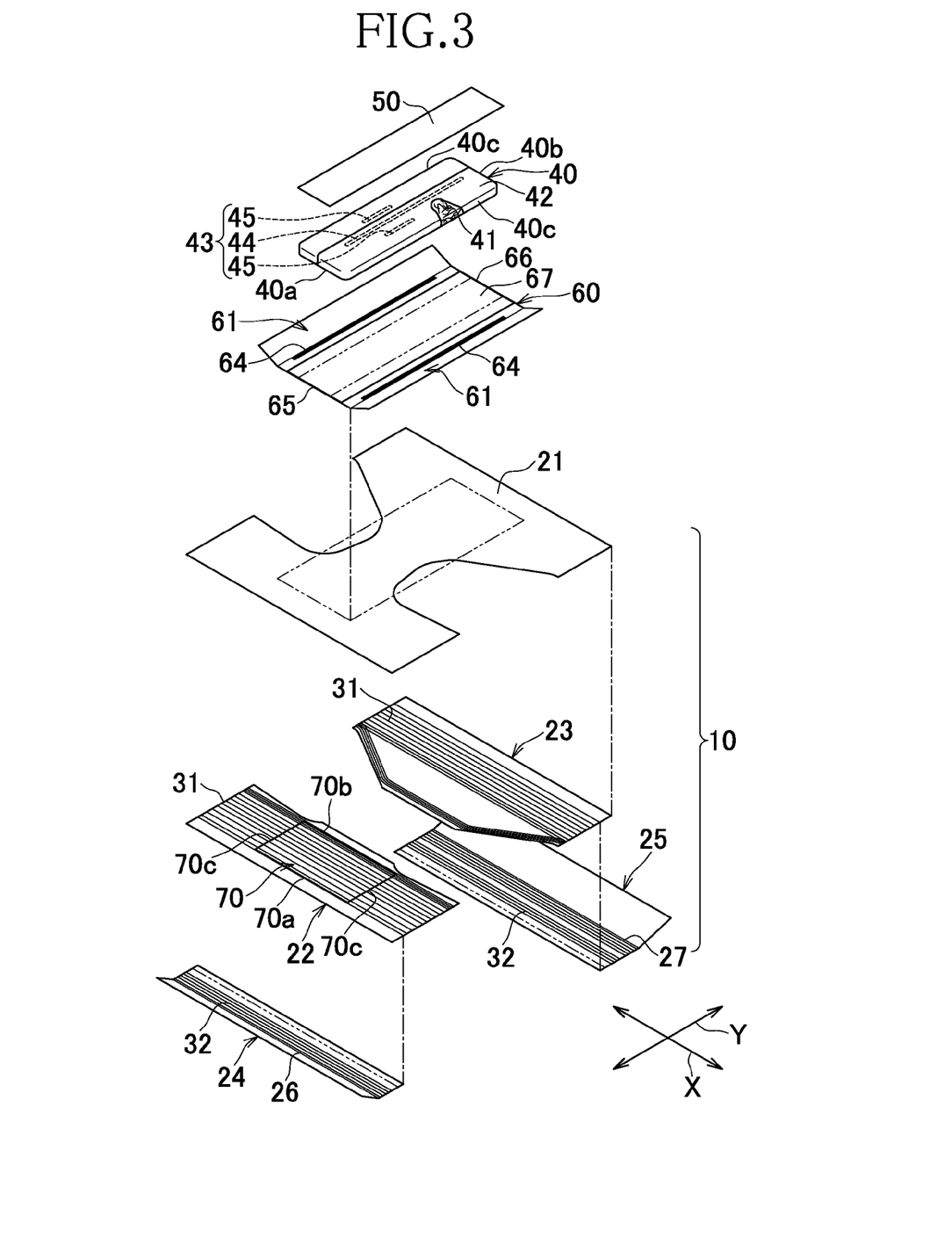
FIG. 3 is an exploded perspective view of the diaper.

Referring to FIGS. 2 and 3, the diaper 1 has a longitudinal center line 2-2 bisecting a dimension in the transverse direction X and a transverse center line 3-3 bisecting a dimension in the longitudinal direction Y wherein the diaper 1 is symmetric about the longitudinal center line 2-2. In these FIGS. 2 and 3, respective elastic members are illustrated in a stretched state against their contractile force.

The chassis 10 includes an interior sheet 21 lying on the skin-facing surface to define the front and rear waist regions 11, 12 and the crotch region 13, front and rear exterior sheets 22, 23 overlaid on the exterior surface side of the interior sheet 21 in a manner that these front and rear exterior sheets 22, 23 may be spaced apart from each other in the longitudinal direction Y, and front and rear waist end covers 24, 25 folded along fold lines 26, 27 extending in the transverse direction X so as to cover the interior sheet 21 and the front and rear exterior sheets 22, 23, respectively. The front exterior sheet 22 defines the front waist region 11 and the rear exterior sheet 23 defines the rear waist region 12 and a part of the crotch region 13. As material for the interior sheet 21, the front and rear exterior sheets 22, 23 and the waist end covers 24, 25, various types of fibrous nonwoven fabrics, for example, thermally adhesive spunbond fibrous nonwoven fabrics having a mass per unit area in a range of about 10 to about 40 g/m², preferably in a range of about 13 to about 20 g/m². a fiber density in a range of about 0.03 to about 0.10 g/m³, preferably in a range of about 0.04 to about 0.09 g/m³ may be used.

Figure 4:
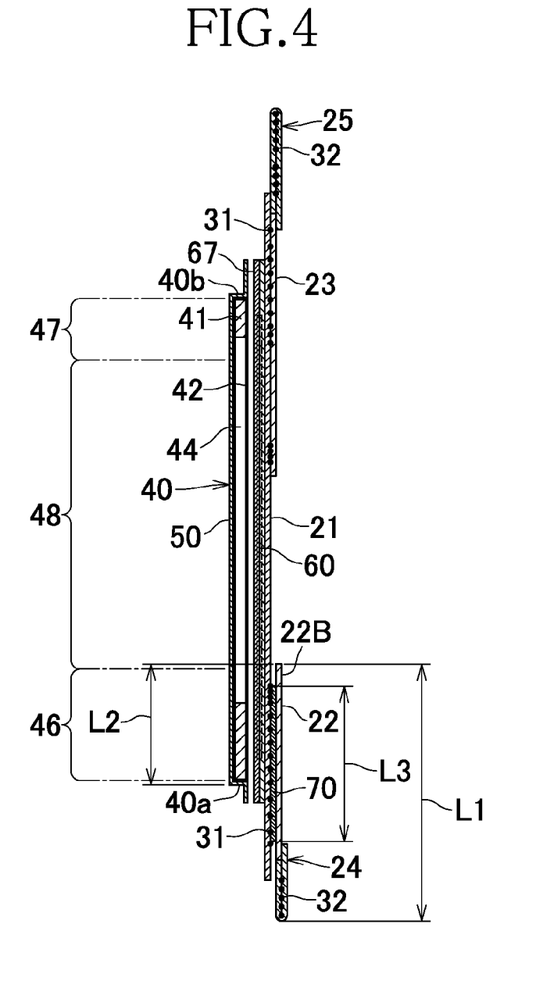
FIG. 4 is a sectional view taken along line IV-IV in FIG. 2.

Referring to FIG. 4 in addition, a plurality of elastic members 31 extending in the transverse direction X are contractibly secured under tension between the interior sheet 21 and the front and rear exterior sheets 22, 23. The front and rear waist end covers 24, 25 are provided within respective sleeves formed by folding these end covers with a plurality of elastic members 31, 32 contractibly secured under tension so as to extend in the transverse direction X. As material for these elastic members 31, 32, for example, thread-, strand- or string-like elastic member having a fineness in a range of about 470 to about 1240 dtex may be used and may be secured, for example, at a stretch ratio in a range of about 1.5 to about 3.5.

On the inner side of the interior sheet 21, an absorbent structure 40 is disposed. The absorbent structure 40 includes front and rear end edges 40a, 40b extending in the transverse direction X, both side edges 40c extending in the longitudinal direction Y, liquid-absorbent core material 41 and a wrapping sheet 42 such as tissue paper to wrap the core material 41. The core material 41 is formed with recesses 43 each boring the core material 41 in its thickness direction and extending in the longitudinal direction Y. The recesses 43 include a central recess 44 extending in the longitudinal direction X along the longitudinal center line 2-2 across the crotch region 13 into the front and rear waist regions 11, 12 and a pair of lateral recesses 45 spaced apart outward from the central recess 44 in the transverse direction X. These lateral recesses 45 have a dimension in the longitudinal direction Y smaller than that of the central recess 44 and are biased toward the front end edge 40a in the crotch region 13.

Figure 5:
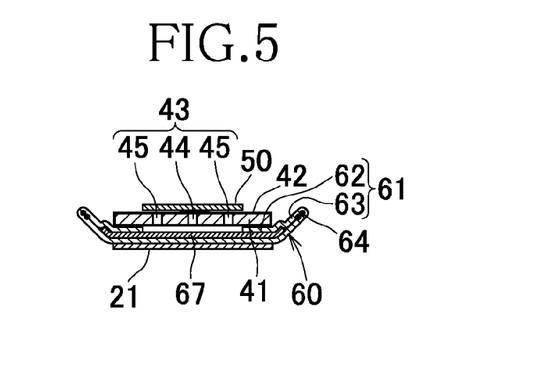
FIG. 5 is a sectional view taken along line V-V in FIG. 2.

A dimension in the transverse direction X between the central recess 44 and each of the lateral recesses 45 is preferably in a range of about 5 to about 20 mm and, for of the present embodiment, this dimension is about 8 mm. A dimension in the longitudinal direction Y of the central recess 44 is preferably in a range of about 200 to about 400 mm and, for the present embodiment, this dimension is about 330 mm. A dimension in the longitudinal direction Y of the lateral recess 45 is preferably in a range of about 50 to 400 mm and, for the present embodiment, this dimension is about 80 mm. As the core material 41, a mixture of wood fluff pulp and superabsorbent polymer particles and optionally any other substances may be used. A mass per unit area of wood fluff pulp is preferably in a range of about 0 to 500 g/m² and, for the present embodiment, this mass per unit area is about 300 g/m². A mass per unit area of superabsorbent polymer particles is preferably in a range of about 0 to about 500 g/m² and, for the present embodiment, this mass per unit area is about 250 g/m². FIG. 5 illustrates the recesses 43, 44 in which the core material does not exist in the thickness direction, but a little amount of the core material may exist on the bottoms of these recesses. The absorbent structure 40 may be provided with these recesses 43, 44 to facilitate the absorbent structure 40 to bend along these recesses 43.44, thereby coming in close contact with the wearer and to absorb body exudates effectively.

Figure 7:
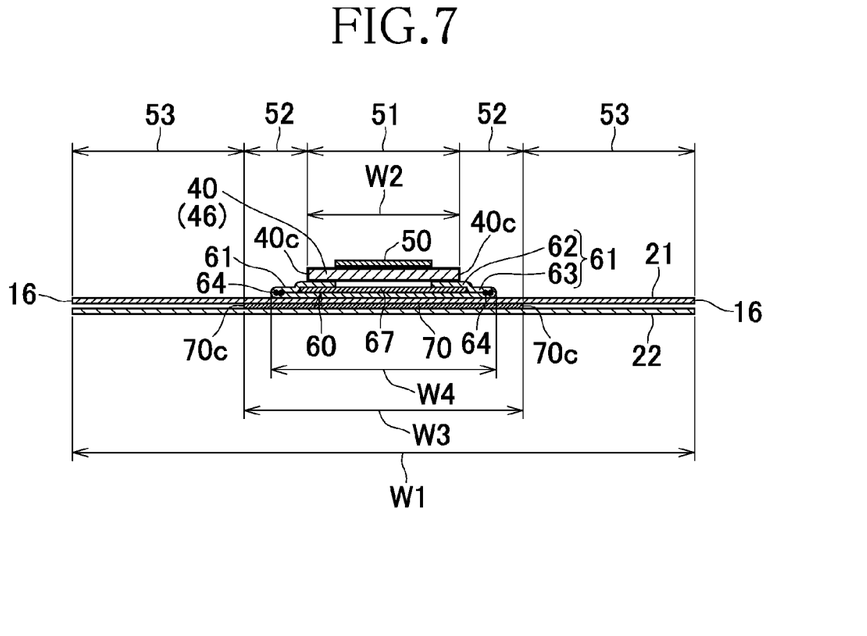
FIG. 7 is a sectional view taken along line VII-VII in FIG. 2.

Referring again to FIGS. 2 and 3, the absorbent structure 40 extends in the longitudinal direction Y across the crotch region 13 into the front and rear waist regions 11, 12 to the front and rear end edges 40a, 40b thereof and, in this way, includes a front end portion 46 overlapping with the front waist region 11, an rear end portion 47 overlapping with the rear waist region 12 and an intermediate portion 48 extending between these front and rear end portions 46, 47 and overlapping with the crotch region 13. Referring to FIG. 7 in addition, a dimension W2 in the transverse direction X of the front end portion 46 is preferably in a range of about 20 to about 30% of a dimension W1 in the transverse direction X of the front waist region 11. For the present embodiment, the dimension W2 in the transverse direction X of the front end portion 46 of the absorbent structure 40 is about 135 mm, the dimension W1 in the transverse direction X of the front waist region 11 is about 580 mm and the dimension W2 is about 23% of the dimension W1.

Referring to FIGS. 2 and 4, a dimension L2 in the longitudinal direction Y of the front end portion 46 is preferably in a range of about 30 to about 60% of a dimension L1 in the longitudinal direction Y of the front waist region 11. For the present embodiment, the dimension L2 in the longitudinal direction Y of the front end portion 46 of the absorbent structure 40 is about 100 mm, the dimension L1 in the longitudinal direction Y is about 230 mm and the dimension L2 is about 43% of the dimension L1.

Considering that the dimension W2 is usually about 30% or more of the dimension W1 and the dimension L2 is usually about 60% or more, the dimension of the front end portion 46 is relatively small in the diaper 1 for the present embodiment.

The dimensions in the longitudinal direction Y and the transverse direction X are the dimensions measured in the state as the respective sheets and the other components are flattened against the contractile forces of the elastic members 31, 32 and cuff-elastic members 64 to be hereinafter described.

The absorbent structure 40 is provided on an absorbent surface with a body-side liner 50 and on a bottom surface thereof with a barrier sheet 60 adapted to define gasket-cuffs 61. Referring to FIG. 3, the barrier sheet 60 has both laterals adapted to be folded back, thereby forming sleeves within which respective cuff-elastic members 64 extend in the longitudinal direction Y and are contractibly secured under tension. In this way, the gasket-cuffs 61 are formed. The gasket-cuffs 61 include, in regions thereof overlapping with the absorbent structure 40, a pair of proximal portions 62 bonded to the absorbent structure 40 and the interior sheet 21 and, in regions thereof extending outward in the transverse direction X from both side edges 40c thereof, a pair of distal portions 63 not bonded to the interior sheet 21. The cuff-elastic members 64 are present in the distal portions 63 and, under contractile force thereof, the distal portions 63 are spaced away from the interior sheet 21 toward the crotch of the diaper wearer. The gasket-cuffs further include front and rear end portions 65, 66 extending in the transverse direction X which are bonded to the interior sheet 21 on the outer sides in the transverse direction X of the absorbent structure 40.

With the gasket-cuffs 61 described above, the distal portions 63 are spaced apart upward from the interior sheet 21 under the contractile force of the cuff-elastic members 64 so as to be put in close contact with the thighs of the wearer, thereby preventing body exudates from leaking (See FIG. 5).

Between the barrier sheet 60 and the absorbent structure 40, a leakage-barrier sheet 67 formed of an air-permeable plastic film is disposed to prevent body exudates once having been absorbed in the absorbent structure 40 from leaking out therefrom. The leakage-barrier sheet 67 extends outward in the transverse direction X from the absorbent structure 40 but is located on the inside of the cuff-elastic members 64. With such an arrangement, it is possible to avoid a possibility that regions of the respective distal portions 63 including the cuff-elastic members 64 might have stiffness increased due to the leakage-barrier sheet 67, thereby protecting the wearer's skin against uncomfortable irritation.

Figure 6:
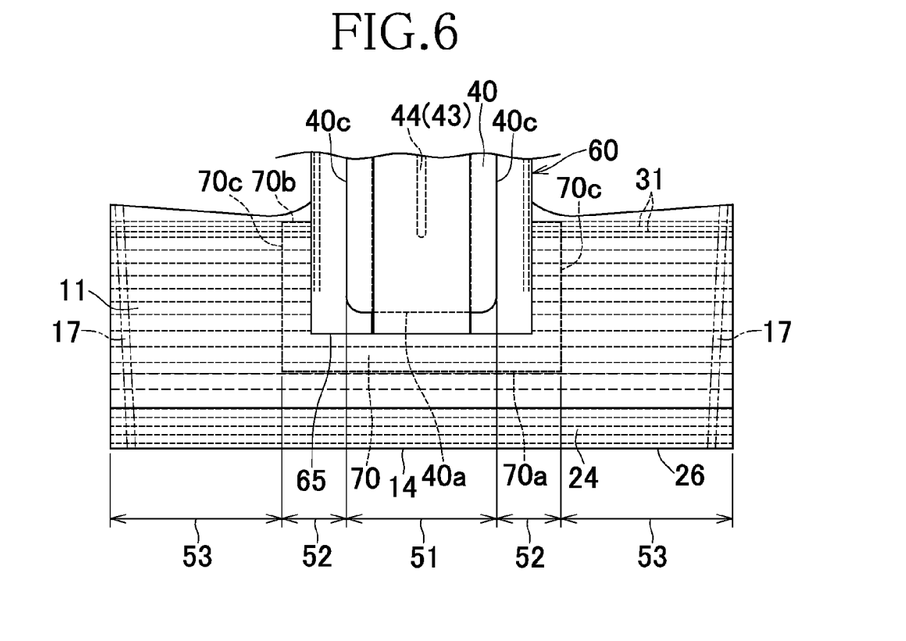
FIG. 6 is a plan view of the front waist region of the diaper in a flatly developed state.

Between the interior sheet 12 and the front exterior sheet 22, a hardly see-through panel 70 is disposed so as to overlap with the front end portion 46 of the absorbent structure 40. The hardly see-through panel 70 has front and rear end edges 70a, 70b extending in the transverse direction X and opposed to each other in the longitudinal direction Y and both side edges 70c extending in the longitudinal direction Y and opposed to each other in the transverse direction X. Referring to FIGS. 2 and 6, both side edges 70c lie on the outer sides in the transverse direction X of both side edges of the absorbent structure 40 and on the outer sides in the transverse direction X of the respective distal portions 63 of the gasket cuffs 61. In other words, a dimension W3 in the transverse direction X of the hardly see-through panel 70 is preferably larger not only than the dimension W2 of the front end portion 46 but also than a dimension W4 in the transverse direction X between a pair of the distal portions 63. For the present embodiment, the dimension W3 is about 260 mm and the dimension W4 is about 200 mm.

Referring to FIGS. 2 and 4, a dimension L3 in the longitudinal direction Y of the hardly see-through panel 70 is preferably larger than the dimension L2 of the front end portion 46 of the absorbent structure 40. For the present embodiment, the dimension L3 is about 160 mm. The dimensions in the longitudinal direction Y and the transverse direction X of the hardly see-through panel 70 are the dimension in the longitudinal direction Y of both side edges 70c and the dimension in the transverse direction X of the front end edge 70a measured in a state of the hardly see-through panel 70 having been flatly developed in the longitudinal direction Y and the transverse direction X against contractile force of the elastic members 31, 32 and 64.

Referring to FIGS. 6 and 7, in both side edge portions 16 of the front waist region 11, the interior sheet 21 and the front exterior sheet 22 are laminated and, in a central portion in the transverse direction X of the front waist region 11, the hardly see-through panel 70 is interleaved and bonded between these two sheets 21, 22. On the inner side of the central portion in the transverse direction X, the gasket cuffs 61 are bonded to the interior sheet 21 and, further inner side in the transverse direction X of the gasket cuffs 61, the leakage-barrier sheet 67 and the absorbent structure 40 are laminated in addition to these sheets. In this manner, from both side edge portions 16 toward the inner side as viewed in the transverse direction X, the number of the constituent members to be laminated gradually increases.

In the diaper 1 arranged in such a manner, the front waist region 11 includes a first region 51 in which the chassis 10, the absorbent structure 40 and the hardly see-through panel 70 are laminated, a pair of second regions 52 being adjacent to outer sides in the transverse direction X of the first region 51, in which the chassis 10 and the hardly see-through panel 70 are laminated, and a pair of third regions 53 being adjacent to outer sides in the transverse direction X of the respective second regions 52. In the first through third regions 51, 52, 53, the number of the sheet members laminated in the respective regions are different and total luminous transmittances TT are different depending on the respective regions. A following TABLE 1 indicates total luminous transmittances of the respective regions 51, 52, 53 in the present embodiment having been obtained by a measuring method as will be described later. TABLE 1 indicates also differential average total luminous transmittance between the first region 51 and the second region 52 which are adjacent in the transverse direction X (a value TT2 of the second region 52—a value TT1 of the first region 51) and a differential average total luminous transmittance between the second region 52 and the third region 53 (a value TT3 of the third region 53—a value TT2 of the second region 52). The measurement for each of the regions was made ten times and the average values of the measurement results were recorded as the average total luminous transmittances of the respective regions 51, 52, 53.

TABLE 1

|  | Light transmittance (%) in $1^{st}$ region 51 | Light transmittance (%) in $2^{nd}$ region 52 | Light transmittance (%) in $3^{rd}$ region 53 | Light transmittance differential between $1^{st}$ and $2^{nd}$ regions 51, 52 | Light transmittance differential between $2^{nd}$ and $3^{rd}$ regions 52, 53 |
|---|---|---|---|---|---|
| 1 | 5.08 | 29.88 | 57.73 | 24.8 | 27.85 |
| 2 | 5.2 | 28.09 | 56.57 | 22.89 | 28.48 |
| 3 | 4.09 | 29.1 | 61.27 | 25.01 | 32.17 |

TABLE 1-continued

|   | Light transmittance (%) in 1st region 51 | Light transmittance (%) in 2nd region 52 | Light transmittance (%) in 3rd region 53 | Light transmittance differential between 1st and 2nd regions 51, 52 | Light transmittance differential between 2nd and 3rd regions 52, 53 |
|---|---|---|---|---|---|
| 4 | 3.23 | 27.6 | 58.93 | 24.37 | 31.33 |
| 5 | 6.23 | 29.55 | 62.01 | 23.32 | 32.46 |
| 6 | 5.43 | 29.87 | 58.43 | 24.44 | 28.56 |
| 7 | 3.02 | 27.6 | 62.84 | 24.58 | 35.24 |
| 8 | 4.89 | 28.56 | 59.64 | 23.67 | 31.08 |
| 9 | 6.03 | 30.05 | 61.21 | 24.02 | 31.16 |
| 10 | 5.42 | 27.43 | 59.99 | 22.01 | 32.56 |
| Mean values | 4.86 | 28.77 | 59.86 | 23.91 | 31.09 |

<Measuring Method for Average Total Luminous Transmittance>

The total luminous transmittance was measured with use of Haze/turbidimeter NDH-300A manufactured by Nippon Denshoku Industrial Co., Ltd. (Power source was turned ON 30 minutes before the measurement). Ten test pieces (including about six elastic members 31 on the side of the crotch region 13) each having a dimension of 40 mm in the longitudinal direction Y and a dimension of 50 mm in the transverse direction X were prepared by cutting out from the diapers 1. An average value of total luminous transmittances calculated from measured values on these ten test pieces was recorded as the average total luminous transmittance (%). Considering that the front waist region 11 as the measuring object includes the elastic members 31 attached thereto under tension, when the test piece was cut out from the diaper 1, the dimensions were measured in a state of the front waist region 11 flatly developed in the longitudinal direction Y as well as in the transverse direction X against the contractile force of the elastic members. In a similar way, the test piece flatly developed in the longitudinal direction Y as well as in the transverse direction X was set in the turbidimeter and measured in such state. For the present embodiment, the test piece includes six elastic members 31.

As indicated in TABLE 1, the average total luminous transmittance TT1 in the first region 51 was 4.86%, the average total luminous transmittance TT2 in the respective second regions 52 is 28.77% and the average total luminous transmittance TT3 in the respective third regions 53 was 59.86%. The average total luminous transmittance in the first region 51 was 4.86%, and therefore, the wearer's skin was not seen through from outside in the existence region of the absorbent structure 40. In the non-existence region of the absorbent structure 40 defined on the outside in the transverse direction X of the absorbent structure 40, the average total luminous transmittance is relatively high and the wearer's skin might be seen through. However, for the present embodiment, the hardly see-through panel 70 extended outward in the transverse direction X beyond the absorbent structure 40 so that the average total luminous transmittance was be decreased to a level at which the wearer's skin was not seen through from the outside without enlarging a width dimension of the absorbent structure 40 beyond necessity with the intention of preventing the wearer's skin from being seen through from the outside.

In this way, not only in the existence region but also in the non-existence region of the absorbent structure 40, the wearer's skin was not seen through at all or hardly seen through. Consequently, the wearer got free of a feeling of embarrassment on concern that the wearer's buttocks might be seen through and can wear the diaper 1 with an easy conscience. In addition, the wearer's skin was hardly seen through also in the non-existence region of the absorbent structure 40. For this reason, the wearer or the helper for wearing had an illusion as if an absorbent area of the absorbent structure was enlarged, making for the wearer or the helper for wearing to cast a feeling of uncertainty for an absorption capacity of the absorbent structure 40 aside.

As the result of measurement of the total luminous transmittance in the respective regions 51, 52, 53, the differential average total luminous transmittance between the first region 51 and the second region 52 (a value TT2 of the second region 52—a value TT1 of the first region 51) was 23.91% and the differential average total luminous transmittance between the second region 52 and the third region 53 (a value TT3 of the third region 53—a value TT2 of the second region 52) was 31.09%. The measurement result such that the differential average total luminous transmittance between each pair of the regions adjacent in the transverse direction X is within a range of 20 to 30% ensures that there is no significant color shade difference due to a differential luminous transmittance between each pair of the regions adjacent in the transverse direction X and no distinct border line between each pair of the adjacent regions is visually recognized from the outside. The measurement result such that the differential average total luminous transmittance between the first region 51 and the second region 52 is smaller than that between the second region 52 and the third region 53 ensures the existence region of the absorbent structure 40 to be not distinct from the other portions in the front waist region 11. Furthermore, the number of the constituent members gradually decreases and the luminous transmittance correspondingly rises from the first region 51 to the third regions 53 outward in the transverse direction X. In consequence, the color shade gradationally lighten little by little from the first region 51 to the third region 53 in the transverse direction X and such gradation contributes to a good appearance of the diaper from a viewpoint of design.

To ensure such effect, the differential total luminous transmittance between the first region 51 and the second region 52 (a value TT2 of the second region 52—a value TT1 of the first region 51) is in a range of about 0 to about 30%, preferably in a range of about 20 to about 30% and the differential total luminous transmittance between the second region 52 and the third region 53 (a value TT3 of the third region 53—a value TT2 of the second region 52) is in a range of about 0 to about 45%, preferably in a range of about 25 to about 45%. If these values exceed the permissible maximum values, the boundary between each pair of the adjacent regions may be visually recognized from the outside rather distinctly, creating a feeling of strangeness from the standpoint of appearance. The total luminous transmittance of the first region 51 preferably at least 5% or higher. The total luminous transmittance less than 5% will make the diaper 1 as a whole seem thicker than it is and may give the impression that the diaper 1 might be inferior in breathability. The measurement was conducted on the front waist region 11 including a plurality of elastic members 31 and, for the chassis 10 not including such plurality of the elastic members, the total luminous transmittance will be correspondingly higher. However, the differential total luminous transmittances between the respective pairs of the adjacent regions 51, 52, 53 are not remarkably different from these for the present embodiment. In this manner, the advantageous effect similar to that for the present embodiment may be ensured.

The front waist region 11 has the elastic members 31 extending in the transverse direction X attached thereto and the front waist region 11 as a whole constricts in the transverse direction X under contraction of these elastic members 31. Compared to the third region 53 merely defined by the laminate of the interior sheet 21 and the front exterior sheet 22, the first region 51 additionally includes the absorbent structure 40 laminated on the interior sheet 21 and the front exterior sheet 22 has correspondingly higher stiffness. If the second regions 52 are not present, a differential stiffness will be apt to create sharp difference in level between the first region 51 and the third regions 53 as the sheets constrict and a desired effect of close contact with the wearer's skin will be deteriorated. However, for the present embodiment, the respective second regions 52 in which the barrier sheet 60 and the hardly see-through panel 70 are laminated are provided on the outsides in the transverse direction X of the absorbent structure 40 so that the stiffness may increase stepwise from the outside toward the inside in the transverse direction X. In this way, the differential stiffness relative to the existence region of the absorbent structure 40 may be reduced. In this way, it is possible to restrict a possibility that a sharp difference in level might be formed due to contraction of the elastic members.

An average bending stiffness B1 in the transverse direction X of the second region 52 is in a range of about 0.4 to about 1.2 gf×cm/cm and, for the present embodiment, in a range of about 0.65 gf×cm/cm. An average bending stiffness B2 in the transverse direction X of the third region 53 defined by only the laminate of the interior sheet 21 and the exterior sheet 22 without lamination of the hardly see-through panel 70 is in a range of about 0.2 to about 0.6 gf×cm/cm and, for the present embodiment, in a range of about 0.28 gf×cm/cm. In this manner, it is possible to enhance the bending stiffness particularly in the transverse direction X by laminating the hardly see-through panel 70, thereby lessening a differential stiffness relative to the absorbent structure 40 and to restrict any sharp difference in level due to contraction of the elastic members.

An average bending stiffness B1 in the transverse direction X of the second region 52 is preferably in a range of about 150 to about 300% of an average bending stiffness B2 of the third region 53. For the present embodiment, the average bending stiffness B1 is about 232% of the average bending stiffness B1. When the average differential bending stiffness between these regions is higher than 300%, there is a possibility that a sharp difference in level might be created between these regions due to contraction of the elastic members and when the average differential bending stiffness is less than 150%, a stiffness of the diaper 1 as a whole will increase and a desired flexibility may be deteriorated.

<Measuring Method for Bending Stiffness>

The bending stiffness was measured with use of Pure Bending Tester KES FB-2 manufactured by KATO TECH CO., LTD. From common regions of the diapers 1, test pieces each having a dimension in the longitudinal direction Y of 50 mm and having a dimension in the transverse X of 100 mm and test pieces each having a dimension in the longitudinal direction Y of 100 mm and a dimension in the transverse direction X of 50 mm were prepared. One end in the longitudinal direction of the test piece was held by one of a pair of chucks and the end in the longitudinal direction of the test piece was held by the other chuck. The test piece was bent as the one chuck was rotated around the other chuck so as to bend the test piece and then a bending stiffness of this test piece was measured with use of a torque detector. The bending stiffness was measured more than once for each test piece and an average value was calculated for each test piece. Then two groups of test pieces each including five test pieces were prepared and average measurement values were recorded as the average bending stiffness (B1, B2) in the transverse direction X. Considering that the front waist region 11 used for the measurement includes the elastic members 31 attached thereto under tension, the front waist region 11 was flatly developed in the longitudinal direction Y as well as in the transverse direction X against the contractile force of these elastic members for making the measurement.

The hardly see-through panel 70 may be located so as to overlap with the front end portion 46 of the absorbent structure 40 to enhance stiffness in the front end portion 46, thereby preventing the absorbent structure 40 from contracting in the transverse direction X under contraction of the elastic members 31. Whereby it is possible to prevent the central recess 44 extending in the front end portion 46 from unacceptably contracting in the transverse direction X and to maintain the original configuration of this recess. If the recesses contract in the transverse direction X so significantly that it becomes impossible to maintain the original configuration, it will be impossible for the absorbent structure 40 to be bent along the recesses and to be put in close contact with the wearer's skin. The present embodiment makes it possible to prevent such problem. Furthermore, formation of the recesses makes it possible to enlarge the absorbent area of the absorbent structure 40 and also to prevent an area loss of the absorbent area as far as the configurations of these recesses are maintained. Arrangement of the central recess 44 so as to extend into the front end portion 46 makes it possible to keep the absorbent structure 40 in close contact with the wearer's skin in the front waist region 11, thereby preventing body exudates from leaking from the front waist region 11.

While the characteristics and the technical effects relating to the total luminous transmittance and the stiffness in the transverse direction X in the first, second and third regions 51, 52, 53 in the front waist regions 11 have been described above, it is also possible to located the hardly see-through panel 70 not in the front waist region 11 but only in the rear waist region 12 or in both the front and rear waist regions 11, 12 to ensure the similar technical effects.

According to the present embodiment, the inner end portion 22B of the front exterior sheet 22 in the crotch region 13 is curved toward the longitudinal center line 2-2 so that the dimension thereof in the longitudinal direction Y may be reduced. Considering that the inner end portion 22B is the portion defining the leg-openings and kept in close contact with the wearer's thighs, the inner end portion 22B is curved in conformity to the wearer's thighs. With such an arrangement, the hardly see-through panel 70 is located further outside the region of the inner end portion 22B lying at the outermost position in the longitudinal direction Y. In this way, it is possible to prevent the hardly see-through panel 70 from coming in contact with the wearer's skin. The dimension between both side edges 70c of the hardly see-through panel 70 is dimensioned to be larger than the minimum dimension in the transverse direction X of the chassis 10, i.e., the dimension in the transverse direction X of the crotch region 13 in the present embodiment. With such dimensioning, it is possible to prevent the hardly see-through panel 70 from coming in contact with the wearer's skin in the transverse direction X also.

As material for the hardly see-through panel 70, moisture-permeable but liquid-impermeable plastic films having a total luminous transmittance at least lower than those of the front and rear exterior sheets 22, 23, a mass per unit area in a range of about 10 to about 30 g/m$^2$, preferably in a range of about 14 to about 25/m$^2$ and mixed or coated with total luminous transmittance suppressor such as delustering agent may be used. Specifically, polyolefin resins may be mixed with inorganic fillers such as titanium oxide (TiO2) having an effect as the total luminous transmittance suppressor and subjected to a stretching process. In this regard, moisture-permeability as well as liquid-impermeability is not essential. However, use of the liquid-impermeable plastic films makes leakage-prevention for body exudates more reliable. As the hardly see-through panel, it is also possible to use fibrous nonwoven fabrics or laminate of plastic films and fibrous nonwoven fabrics. As the fibrous nonwoven fabrics, both liquid-permeable fibrous nonwoven fabrics and poorly-liquid-permeable fibrous nonwoven fabrics may be used. Though the fibrous nonwoven fabrics may be used alone, in this case, melt blown fibrous nonwoven fabrics impregnated with titanium oxide may be used.

While the hardly see-through panel 70 is located in the front waist region 11 according to the present embodiment, it is also possible to dispose this in the rear waist region 12 or in both these waist regions. While the present embodiment has been described with respect to the pull-on diaper in which the front and rear waist regions 11, 12 are previously joined together along the respective side edges, the present invention is applicable also to open type diapers.

The disclosure of the present invention as has been described hereinabove may be arranged at least as follows: A wearing article having a longitudinal direction and a transverse direction being orthogonal to the longitudinal direction and including a chassis having a skin-facing surface and a non-skin-facing surface lying on a side opposite to the skin-facing surface, a first waist region corresponding to one of front and rear waist regions, a second waist region corresponding to another of the front and rear waist regions and a crotch region extending between the first and second waist regions and an absorbent structure disposed on the skin-facing surface of the chassis and extending in the longitudinal direction across the absorbent structure at least into the first waist region.

The present invention includes the following features: a region of the absorbent structure overlapping with the first waist region has a dimension in the transverse direction corresponding to 20 to 30% of a dimension in the transverse direction of the first waist region;

the first waist region is provided with a hardly see-through panel overlapping with the absorbent structure and includes a first region in which the chassis, the absorbent structure and the hardly see-through panel are laminated, second regions adjacent on both outsides in the transverse direction of the first region, in which the chassis and the hardly see-through panel are laminated and third regions adjacent on both outsides in the transverse direction of the respective second regions and only the chassis is included; and a differential total luminous transmittance between the first region and the second regions is smaller than a differential total luminous transmittance between the second region and the third region.

The present invention as set forth may include embodiments at least as will be described below:

(1) A differential total luminous transmittance between the first region and the second region is in a range of 0 to 30% and a differential total luminous transmittance between the second region and the third region is in a range of 0 to 45%.

(2) The wearing article further includes a pair of gasket cuffs located on the skin-facing surface of the chassis and extending across the crotch region in the longitudinal direction into the first and second waist regions;

the gasket cuffs include first and second end portions extending in the transverse direction and bonded to the first and second waist regions, proximal portions extending in the longitudinal direction and bonded to the chassis, distal portions lying on outsides of the respective proximal portions in the transverse direction and adapted to be spaced apart from the chassis and elastic members attached to the distal portions so as to contractible in the longitudinal direction;

the distal portions lie on the outsides in the transverse direction of the absorbent structure; and both side edges opposite in the transverse direction of the hardly see-through panel lie on the outsides in the transverse direction of the distal portions.

(3) The hardly see-through panel has first and second end edges extending in the transverse direction and the first end edge lies outside in the longitudinal direction of the absorbent structure lying in the first region.

(4) The first waist region is provided with a plurality of elastic members extending in the transverse direction and contractibly secured thereto under tension and at least partially overlapping with the absorbent structure and the hardly see-through panel in the first region.

(5) A bending stiffness of the second region is in a range of 150 to 300% of a bending stiffness of the third region.

The constituent members of the diaper 1 are not limited to those described in the present specification but the other various types of material widely used in the relevant technical field may be used without limitation unless otherwise stated. The present invention is applicable to open-type diapers as well, in which the front and rear waist regions are not joined to each other along the seams.

Terms "first", "second" and "third" used in the specification and claims of the present invention are used merely to distinguish the similar elements, similar positions or the other similar items.

REFERENCE SIGNS LIST

1 diaper (wearing article)
10 chassis
11 front waist region (one of first and second waist regions)
12 rear waist region (the other of first and second waist regions)
13 crotch region
31 elastic members
40 absorbent structure
51 first region
52 second region
53 third region
61 gasket cuffs
62 proximal regions 63 distal regions
64 cuff elastic members
65 front end (first end)
66 rear end (second end)
70 hardly see-through panel
70a front end edge (first end edge)
70b rear end edge (second end edge)
70c both side edges
X transverse direction
Y longitudinal direction

The invention claimed is:

1. A wearing article having a longitudinal direction and a transverse direction being orthogonal to the longitudinal direction and including a chassis having a skin-facing surface and a non-skin-facing surface lying on a side opposite to the skin-facing surface, a first waist region corresponding to one of front and rear waist regions, a second waist region corresponding to another of the front and rear waist regions and a crotch region extending between the first and second waist regions and an absorbent structure disposed on the skin-facing surface of the chassis and extending in the longitudinal direction across the absorbent structure at least into the first waist region, wherein:
   a region of the absorbent structure overlapping with the first waist region has a dimension in the transverse direction corresponding to 20 to 30% of a dimension in the transverse direction of the first waist region;
   the first waist region is disposed with a hardly see-through panel overlapping with the absorbent structure and includes a first region in which the chassis, the absorbent structure and the hardly see-through panel are laminated, second regions adjacent on both outsides in the transverse direction of the first region, in which the chassis and the hardly see-through panel are laminated and third regions adjacent on both outsides in the transverse direction of the respective second regions and only the chassis is included; and
   a differential total luminous transmittance between the first region and the second regions is smaller than a differential total luminous transmittance between the second region and the third region.

2. The wearing article according to claim 1 wherein a differential total luminous transmittance between the first region and the second region is in a range of 0 to 30% and a differential total luminous transmittance between the second region and the third region is in a range of 0 to 45%.

3. The wearing article according to claim 2, wherein the wearing article further includes a pair of gasket cuffs disposed on the skin-facing surface of the chassis and extending across the crotch region in the longitudinal direction into the first and second waist regions;
   the gasket cuffs include first and second end portions extending in the transverse direction and bonded to the first and second waist regions, proximal portions extending in the longitudinal direction and bonded to the chassis, distal portions lying on outsides of the respective proximal portions in the transverse direction and adapted to be spaced apart from the chassis and elastic members attached to the distal portions so as to contractible in the longitudinal direction;
   the distal portions lie on the outsides in the transverse direction of the absorbent structure; and
   both side edges opposite in the transverse direction of the hardly see-through panel lie on the outsides in the transverse direction of the distal portions.

4. The wearing article according to claim 3, wherein the hardly see-through panel has first and second end edges extending in the transverse direction and the first end edge lies outside in the longitudinal direction of the absorbent structure lying in the first region.

5. The wearing article according to claim 4, wherein the first waist region is disposed with a plurality of elastic members extending in the transverse direction and contractibly secured thereto under tension at least partially overlapping with the absorbent structure and the hardly see-through panel in the first region.

6. The wearing article according to claim 3, wherein the first waist region is disposed with a plurality of elastic members extending in the transverse direction and contractibly secured thereto under tension at least partially overlapping with the absorbent structure and the hardly see-through panel in the first region.

7. The wearing article according to claim 2, wherein the hardly see-through panel has first and second end edges extending in the transverse direction and the first end edge lies outside in the longitudinal direction of the absorbent structure lying in the first region.

8. The wearing article according to claim 7, wherein the first waist region is disposed with a plurality of elastic members extending in the transverse direction and contractibly secured thereto under tension at least partially overlapping with the absorbent structure and the hardly see-through panel in the first region.

9. The wearing article according to claim 2, wherein the first waist region is disposed with a plurality of elastic members extending in the transverse direction and contractibly secured thereto under tension at least partially overlapping with the absorbent structure and the hardly see-through panel in the first region.

10. The wearing article according to claim 9, wherein a bending stiffness of the second region is in a range of 150 to 300% of a bending stiffness of the third region.

11. The wearing article according to claim 2, wherein a bending stiffness of the second region is in a range of 150 to 300% of a bending stiffness of the third region.

12. The wearing article according to claim 1, wherein the wearing article further includes a pair of gasket cuffs disposed on the skin-facing surface of the chassis and extending across the crotch region in the longitudinal direction into the first and second waist regions;
   the gasket cuffs include first and second end portions extending in the transverse direction and bonded to the first and second waist regions, proximal portions extending in the longitudinal direction and bonded to the chassis, distal portions lying on outsides of the respective proximal portions in the transverse direction and adapted to be spaced apart from the chassis and elastic members attached to the distal portions so as to contractible in the longitudinal direction;
   the distal portions lie on the outsides in the transverse direction of the absorbent structure; and
   both side edges opposite in the transverse direction of the hardly see-through panel lie on the outsides in the transverse direction of the distal portions.

13. The wearing article according to claim 12, wherein the hardly see-through panel has first and second end edges extending in the transverse direction and the first end edge lies outside in the longitudinal direction of the absorbent structure lying in the first region.

14. The wearing article according to claim 13, wherein the first waist region is disposed with a plurality of elastic members extending in the transverse direction and contractibly secured thereto under tension at least partially overlapping with the absorbent structure and the hardly see-through panel in the first region.

15. The wearing article according to claim 12, wherein the first waist region is disposed with a plurality of elastic members extending in the transverse direction and contractibly secured thereto under tension at least partially overlapping with the absorbent structure and the hardly see-through panel in the first region.

16. The wearing article according to claim 12, wherein a bending stiffness of the second region is in a range of 150 to 300% of a bending stiffness of the third region.

17. The wearing article according to claim 1, wherein the hardly see-through panel has first and second end edges extending in the transverse direction and the first end edge lies outside in the longitudinal direction of the absorbent structure lying in the first region.

18. The wearing article according to claim 17, wherein the first waist region is disposed with a plurality of elastic members extending in the transverse direction and contractibly secured thereto under tension at least partially overlapping with the absorbent structure and the hardly see-through panel in the first region.

19. The wearing article according to claim 1, wherein the first waist region is disposed with a plurality of elastic members extending in the transverse direction and contractibly secured thereto under tension at least partially overlapping with the absorbent structure and the hardly see-through panel in the first region.

20. The wearing article according to claim 1, wherein a bending stiffness of the second region is in a range of 150 to 300% of a bending stiffness of the third region.

* * * * *